US008795715B2

(12) United States Patent
Funda

(10) Patent No.: US 8,795,715 B2
(45) Date of Patent: Aug. 5, 2014

(54) COMPOSITIONS OF FAT-SOLUBLE SUBSTANCES

(75) Inventor: Elger Funda, Grenzach-Wyhlen (DE)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 12/820,035

(22) Filed: Jun. 21, 2010

(65) Prior Publication Data

US 2010/0260811 A1    Oct. 14, 2010

Related U.S. Application Data

(62) Division of application No. 11/659,509, filed as application No. PCT/EP2005/008297 on Aug. 1, 2005, now abandoned.

(30) Foreign Application Priority Data

Aug. 19, 2004   (EP) .................................... 04019678

(51) Int. Cl.
*A23K 1/17*       (2006.01)
*A61K 8/02*       (2006.01)
*A61K 9/14*       (2006.01)

(52) U.S. Cl.
USPC ............ 424/442; 424/401; 424/484; 424/488

(58) Field of Classification Search
USPC .................. 424/442, 401, 484, 488; 514/691; 426/89
See application file for complete search history.

(56) References Cited

U.S. PATENT DOCUMENTS

| 2,937,091 | A | * | 5/1960 | Rosenberg ..................... 424/489 |
| 3,110,598 | A |   | 11/1963 | Muller et al. |
| 3,886,294 | A |   | 5/1975 | Emodi et al. |
| 4,522,743 | A |   | 6/1985 | Horn et al. |
| 4,880,646 | A | * | 11/1989 | Lew et al. ....................... 426/93 |
| 5,013,569 | A |   | 5/1991 | Rubin |
| 6,309,677 | B1 |   | 10/2001 | Gorenbein et al. |
| 2003/0064133 | A1 | * | 4/2003 | Blatt et al. ..................... 426/72 |

FOREIGN PATENT DOCUMENTS

| DE | 102 05 362 A1 | 8/2003 |
| GB | 887883 | 1/1962 |
| GB | 2 248 170 | 4/1992 |
| JP | 6-145062 | 5/1994 |
| JP | 6-227961 | 8/1994 |
| JP | 8-116887 | 5/1996 |
| WO | 03/066019 | 8/2003 |

OTHER PUBLICATIONS

International Search Report mailed Dec. 16, 2005 in PCT/EP2005/008297.
Written Opinion mailed Dec. 16, 2005 in PCT/EP2005/008297.

* cited by examiner

*Primary Examiner* — Aradhana Sasan
(74) *Attorney, Agent, or Firm* — Nixon & Vanderhye P.C.

(57) ABSTRACT

The invention relates to novel powderous, water-soluble compositions of fat-soluble substances and aqueous solutions or emulsions thereof, wherein the fat-soluble substance(s) are encapsulated as inner (discontinuous phase) within an outer (continuous) phase of a matrix substance.

9 Claims, No Drawings

COMPOSITIONS OF FAT-SOLUBLE SUBSTANCES

This application is a divisional of commonly owned U.S. application Ser. No. 11/659,509, filed on Feb. 7, 2007 (now abandoned), which is the national phase application under 35 USC §371 of PCT/EP2005/008297, filed Aug. 1, 2005 which designated the US and claims benefit of EP 04019678.4, filed 19 Aug. 2004, the entire contents of which is hereby incorporated by reference.

The present invention relates to novel compositions of fat-soluble substances. More particularly, the present invention relates to novel powderous, water-soluble compositions of fat-soluble substances and aqueous solutions or emulsions thereof. The novel compositions of this invention can be used as additives for food, beverages, animal feeds, cosmetics or drugs to incorporate said fat-soluble ingredients into such items. A particular feature of the novel compositions is the encapsulation of the fat-soluble substance(s) to form an inner (discontinuous) phase within an outer (continuous) phase of a matrix substance.

Thus, in one aspect, the present invention relates to novel compositions comprising
a) a matrix substance forming an outer (continuous) phase; and
b) an inner (discontinuous) phase within said matrix substance which comprises
b1) a fat-soluble physiologically active ingredient which is embedded in
b2) a physiologically acceptable encapsulating substance which is solid at room temperature and, together with said fat-soluble physiologically active ingredient, is homogeneously soluble in an organic solvent.

In a further aspect, the present invention relates to a process for the preparation of the novel compositions as defined above.

In still another aspect, the present invention relates to food or animal feed or supplement therefore, or pharmaceutical or cosmetic formulations comprising a composition as defined above.

The term "fat-soluble active ingredient" as used herein denotes any physiologically active ingredient that is soluble in lipids and insoluble or sparingly soluble in water. Examples of such fat-soluble active ingredients are fat-soluble vitamins, viz., vitamin A, D, E and K and derivatives thereof such as vitamin A esters, e.g. vitamin A acetate and palmitate, and vitamin E esters, e.g. tocopherol acetate; carotenoids and carotenoid derivatives, e.g., are α- or β-carotene, 8'-apo-β-carotenal, 8'-apo-β-carotenoic acid esters such as the ethyl ester, canthaxanthin, astaxanthin, astaxanthin esters, lycopene, lutein, zeaxanthin or crocetin and their derivatives; polyunsaturated fatty acids, e.g. eicosapentaenoic acid, docosahexaenoic acid, arachidonic acid and γ-linolenic acid and/or ethylester.

The term "encapsulating substance" denotes any edible substance, that is solid at application temperature, able to encapsulate the active ingredient and soluble together with the active ingredient in one common solvent. Preferably used are substances, which are commonly used as coating materials. More preferably used are synthetic or natural waxes or wax-like substances, or natural or synthetic edible polymers.

The wax or wax-like substance is preferably selected from among e.g. carnauba wax, candelilla wax, beeswax, rice bran wax, sugar cane wax, japan wax, esparto grass wax, cork wax, guaruma wax, ouricury wax, montan wax, spermaceti, lanolin, hydrated jojoba wax or paraffin wax, fats, hydrogenated fats, fatty acid monoglycerides, polypropylene glycol, polyethylene glycol, fatty acid esters, sucrose fatty acid esters, fatty acids, hydrocarbons and hydrogenated products thereof.

Natural edible polymers are preferably selected from modified (e.g. alkylated) carbohydrates (e.g. starch, pectin, alginate, carrageenan, furcellaran, chitosan, maltodextrin, dextrin derivatives), celluloses and cellulose derivatives (e.g. cellulose acetate, methyl cellulose, hydroxypropyl methyl cellulose), gums or modified (e.g. alkylated) gums (e.g. gum arabic, gum xanthan, gum guar, gum ghatti, gum karaya, gum tragacanth, locust bean gum, gellan gum), resins (e.g. shellac, wood rosin, and tree resins such as copal, damar and elemi), zein. Modification of these polymers may be necessary to improve solubility in organic solvents.

The synthetic polymer is preferably selected from among the synthetic waxes such as polyethylene and polypropylene waxes, coumarene-indene resins, polylactic acid (PLA) and poly(lactic/glycolic) acid (PLGA), acrylic polymers (methacrylic acid copolymers and ammonio methacrylate copolymers), polyorthoesters, polyphosphazenes, polyanhydrides, polyglycolide (PGA), poly(ε-caprolactone), polydioxanone, trimethylene carbonate, poly(β-hydroxybutyrate), poly(γ-ethyl glutamate), poly(DTH iminocarbonate), poly(bisphenol A iminocarbonate) and polycyanoacrylate, especially the acrylic polymers. Polyvinyl alcohol and polyvinylpyrrolidone polymers may also be used.

Preferred encapsulating substances for use in the invention are beeswax, carnauba wax, paraffin wax, polyethylene glycol and hydrogenated fats.

The ratio between active ingredient and encapsulating substance is determined by the amount of encapsulating substance, necessary to protect the active ingredient and by the target content of active ingredient within the formulation. Ratio of active ingredient: encapsulating substance may vary between about 10:1 to about 1:20 preferably between 1:3 and 3:1.

Ratio of (active ingredients+encapsulating substances): matrix is selected according to requirements of the specific formulation. Typical ratios could be e.g. 1:99 (1% forms), 1:9 (10% forms) or 1:1 (50% forms). The amount of matrix is determined by the amount necessary to stabilise the emulsion and to encapsulate the inner (oily) phase.

Matrix components are preferably selected from among carbohydrates (e.g. cellulose, starch, modified starch, dextrin, pectin, alginate, carrageenan, furcellaran, chitosan), gums (e.g. gum arabic, gum xanthan, gum guar, gum ghatti, gum karaya, gum tragacanth, locust bean gum, gellan gum), proteins (e.g. fish, poultry and mammalian gelatine, soy protein, pea protein, zein (from corn) wheat gluten, lupin protein, peanut protein, milk proteins or hydrolysed or modified milk proteins, especially casein or whey proteins, lignins and lignin derivatives (e.g. lignosulfonates, kraft lignins), celluloses and cellulose derivatives (e.g. carboxymethyl cellulose, carboxyethyl cellulose, hydroxypropyl cellulose).

Preferred matrix substances for use in the invention are gelatin, lignosulfonates, milk proteins or hydrolysed milk proteins, plant proteins or hydrolysed plant proteins, or modified starch, especially gelatine, casein and casein hydrolysates, soy protein, hydrolysates thereof, lignosulfonate, physically modified soy protein, starches and modified starches, especially octyl succinyl starch, pectins and carboxymethyl cellulose.

Particularly preferred are matrix substances which provide cold-water soluble compositions, such as lignosulfonate, fish gelatin, milk protein and hydrolysed plant proteins.

As solvent any organic solvent or solvent combination may be used that is able to dissolve active ingredient and encapsulating substance. Volatile Solvents and solvent combinations that are easy to evaporate from the emulsion are preferred. Examples for solvents are isopropanole, hexane, cyclohexane, acetone, methyl ethyl ketone, methylenchloride, chloroform, toluene, tetrahydrofurane, acetic acid ethyl ester.

As will be apparent from the foregoing, the compositions according to the invention comprise a matrix substance as a continuous phase wherein particles (droplets) of an encapsulating substance are distributed. Within said particles (droplets) of the encapsulating substance, the fat-soluble substance is distributed. Such compositions are distinguished from compositions wherein particles of the fat-soluble substance are distributed within a matrix substance (see, e.g. EP 564 989) or compositions wherein the fat-soluble substance is coated with a coating material or compositions according to JP 2004196673 wherein carotenoid-containing solutions are emulsified with coating solutions and subsequent freeze-drying thus producing powders wherein active ingredient and coating agent are distributed in different phases of the emulsion. The compositions of the present invention by virtue of their unique structure and mode of preparation provide superior stability on storage and application and show good bioavailability.

If necessary other components like antioxidants, butylated hydroxy anisole (BHA), butylated hydroxy toluene (BHT), ethoxyquin (6-ethoxy-1,2-dihydro-2,2,4-trimethyl-quinoline), and the like, emulsifiers, such as lecithin plasticisers, stabilisers, humectants like glycerin, sorbitol, polyethylene glycol, protective colloids, buffers, adjuvants can be included into the composition.

The particle size of the inner phase of the compositions according to the present invention is preferably less than 5 µm, more preferably less than 100 µm, e.g. 100 nm to 500 nm. The particle size of the powderous compositions according to the present invention is typically in the range of 50-500 µm.

Active ingredients and encapsulating substances are dissolved in the solvent, preferably with stirring. If required, the solvent may be heated, if necessary under elevated pressure. Emulsifiers and other adjuvants may also be dissolved in the organic solvent.

The matrix compounds are dissolved in water, preferably with stirring. If required, the water may be heated. Emulsifiers and other water-soluble adjuvants may also be dissolved in the aqueous phase.

Organic and aqueous phase are mixed to form an emulsion. Emulsions may be prepared by any suitable method known to the person skilled in the art. Suitable known methods of preparation include emulsification with rotor-stator-systems, high pressure homogenisers or ultrasonic emulsification. To ensure good bioavailability, a small particle size of the active ingredient is required. Therefore, the particle size of the emulsion droplets should preferably be less than 5 µm, more preferably less than 1 µm, more preferably less than 0.5 µm.

Evaporation of the solvent may be performed by any suitable method known to the person skilled in the art. Suitable known methods of evaporation are e.g. thin-film evaporation or falling film evaporation. Evaporation may be done with or without reduced pressure at ambient or elevated temperature as required.

Although product forms described in this invention are preferably used as powders, other formulation types are also possible, e.g. liquid forms, pastes or pellets.

Powderous formulations are preferably produced by spray drying or by beadlet process as described e.g. in U.S. Pat. No. 6,444,227. Other known drying methods may also be used.

Solid forms could e.g. also be produced by extrusion of the emulsion together with a binder.

Liquid forms can be produced by using the emulsion after evaporation of the solvent.

The following Examples illustrate the invention further.

EXAMPLE 1

2.5% Canthaxanthin Spray-Dried Powder.

(a) 330 g of gelatine, 279 g of sucrose, 0.75 g of sorbic acid and 1.50 g of sodium benzoate are added to 330 g of distilled water. The gelatine mixture is solubilised by hydrating overnight at about 50° C.

(b) The following solution is prepared:
Ascorbic acid 2.25 g
EDTA 0.75 g
Sodium lauryl sulfate 12.0 g
Distilled water 105.0 g
This solution is added to the gelatine-sugar solution (a) to form the aqueous phase of the emulsion. The pH of this solution is adjusted to 10.4±0.2 using a 20% w/w sodium hydroxide solution.

(c) An oil phase is prepared from
Canthaxanthin 23.3 g
Butylated hydroxy-toluene (BHT) 22.5 g
dl-α-tocopherol 22.5 g
Beeswax 23.3 g and
Chloroform 525 g
by first dissolving the BHT in dl-α-tocopherol by heating the mixture to 80° C. The solution is cooled to 55° C. and then mixed with the chloroform until a clear solution results. Canthaxanthin and beeswax are added to this solution under nitrogen atmosphere and dissolved.

Both the aqueous and oil phases are heated to about 50°-55° C. The oil phase is added slowly to the aqueous phase using both a high rate of mixing and a high shear force mixer. After the addition is completed, the emulsion temperature is maintained at 55° C. while high speed shear mixing is continued for 15 minutes. The temperature is gradually raised and mixing is continued until all the chloroform has been evaporated. This evaporation is usually completed when the temperature of the emulsion reaches about 75° C.

During the evaporation procedure distilled water is added to the emulsion to maintain a viscosity appropriate to promote the evaporation procedure.

After all the chloroform has been removed, distilled water is added and thoroughly admixed with the emulsion to achieve an emulsion solids content and viscosity suitable for spray-drying. Viscosity of the spraying emulsion should be about 100 mPas The emulsion is spray-dried under standard spray drying conditions using a spray drying tower. Spraying conditions are suitably chosen in a way to keep product temperatur below 80° C.

EXAMPLE 2

10% Canthaxanthin Beadlet.

15 g canthaxanthin and 15 g beeswax are dissolved together with 3 g Ethoxyquin in 600 ml chloroform. 75 g Na-Lignosulfonate is dissolved in 375 ml demineralised water. The pH of this solution is adjusted to 7.5±0.5 using a 20% w/w sodium hydroxide solution. The oil phase is added slowly to the aqueous phase using both a high rate of mixing and a high shear force mixer. After the addition is completed, the emulsion temperature is maintained at 50° C. while high speed shear mixing is continued for 15 minutes. The temperature is gradually raised and mixing is continued until all the chloroform has been evaporated. This evaporation is usually completed when the temperature of the emulsion reaches about 75° C. During the evaporation procedure, distilled water is added to the emulsion to maintain a suitable viscosity.

After all the chloroform has been removed, distilled water is added and thoroughly admixed with the emulsion to achieve an emulsion solids content and viscosity suitable for spraying. The emulsion is then sprayed into a bed of 1 kg of fluidised starch using a lab spraying-pan. Residual starch is removed by sieving.

The invention claimed is:

1. A composition comprising:
   a) a matrix substance forming a continuous phase which is at least one selected from the group consisting of gelatin, a lignosulfonate, a milk protein or a hydrolyzed milk protein, a plant protein or hydrolyzed plant protein and a modified starch; and
   b) an encapsulated active ingredient forming a discontinuous phase within said matrix substance, wherein the encapsulated active ingredient comprises,
      b1) a carotenoid as a fat-soluble physiologically active ingredient, and
      b2) a physiologically acceptable encapsulating substance which is solid at room temperature and in which the fat-soluble physiologically active ingredient b1) is embedded, wherein
   the physiologically acceptable encapsulating substance b2) is at least one selected from the group consisting of beeswax, carnauba wax, paraffin wax, polyethylene glycol and hydrogenated fats; and wherein
   the fat-soluble physiologically active ingredient b1) and the physiologically acceptable encapsulating substance b2) are together homogeneously soluble in a common organic solvent for both b1) and b2), and wherein the encapsulated active ingredient b) is a residue remaining after solvent evaporation of a solution comprising the fat-soluble physiologically active ingredient b1), the physiologically acceptable encapsulating substance b2) and the common organic solvent in which b1) and b2) are soluble.

2. A composition as in claim 1, wherein the carotenoid is astaxanthin or canthaxanthin.

3. A composition as in claim 1 wherein the fat-soluble physiologically active ingredient b1) is a polyunsaturated fatty acid.

4. A composition as in claim 1 in the form of an aqueous emulsion.

5. A composition as in claim 1 in the form of a solid composition.

6. A composition as in claim 5 which is cold-water soluble.

7. A composition as in claim 1 which further comprises at least one auxiliary agent selected from the group consisting of antioxidants, stabilising and emulsifying agents.

8. A composition as in claim 1, which is made by a process which comprises the steps of dissolving the fat-soluble physiologically active ingredient b1) and the encapsulating substance b2) in the common organic solvent for both b1) and b2) to obtain an oily phase, emulsifying the oily phase with an aqueous solution of the matrix substance a), evaporating the common organic solvent, and optionally, converting the emulsion into a solid state composition.

9. A food or animal feed or supplement therefor, or a pharmaceutical or cosmetic formulation comprising a composition as defined in claim 1.

* * * * *